(12) United States Patent
Fischer

(10) Patent No.: US 10,898,170 B2
(45) Date of Patent: Jan. 26, 2021

(54) MICROBIOPSY DEVICE

(71) Applicant: UNIVERSITY OF MASSACHUSETS MEDICAL SCHOOL, Boston, MA (US)

(72) Inventor: Andrew H. Fischer, Stow, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/224,229

(22) Filed: Jul. 29, 2016

(65) Prior Publication Data
US 2018/0014819 A1    Jan. 18, 2018

Related U.S. Application Data

(63) Continuation of application No. PCT/US2015/013823, filed on Jan. 30, 2015.

(60) Provisional application No. 61/934,010, filed on Jan. 31, 2014.

(51) Int. Cl.
*A61B 10/02*        (2006.01)

(52) U.S. Cl.
CPC ...... *A61B 10/0266* (2013.01); *A61B 10/0283* (2013.01)

(58) Field of Classification Search
CPC .... A61B 2010/0208; A61B 2010/0225; A61B 10/0283; A61B 10/02
See application file for complete search history.

(56) References Cited

U.S. PATENT DOCUMENTS

| 4,543,966 A | 10/1985 | Islam et al. | |
| 5,810,744 A * | 9/1998 | Chu | A61B 10/0275 600/567 |
| 6,086,543 A | 6/2000 | Anderson et al. | |
| 2005/0101879 A1* | 5/2005 | Shidham | A61B 10/0283 600/566 |
| 2008/0300507 A1* | 12/2008 | Figueredo | A61B 10/0266 600/567 |

(Continued)

FOREIGN PATENT DOCUMENTS

WO    2014028626 A1    2/2014

OTHER PUBLICATIONS

International Search Report in Parent PCT/US15/13823 dated Apr. 15, 2015, 2 pages.

(Continued)

*Primary Examiner* — Patrick Fernandes
(74) *Attorney, Agent, or Firm* — Milstein Zhang & Wu LLC

(57) ABSTRACT

An improved microbiopsy needle tip is described. The improvement is attributable to the presence of one or more combinations of features, including the use of a Franseen-type needle cutting tip, the provision of a "step-out" in which the collection portion of the biopsy device has a larger diameter than the procuring portion of the device, frictional force on the core of tissue exerted by the distal portion of the needle, which force is provided by the diameter of the distal collection portion of the device having substantially the same diameter as that of the procured core of tissue, the mechanical effects of scaling the needle to small dimensions; and the use of a needle that can be curved to as to sample multiple biopsy sites in close proximity without retracting the needle from the patient.

11 Claims, 12 Drawing Sheets

(56) References Cited

U.S. PATENT DOCUMENTS

2010/0204611 A1\* 8/2010 Zambelli .............. A61B 10/025
  600/567
2012/0165832 A1 6/2012 Costman, Jr. et al.
2013/0053725 A1 2/2013 Beck et al.

OTHER PUBLICATIONS

Written Opinion in Parent PCT/US15/13823 dated Apr. 15, 2015, 5 pages.

\* cited by examiner

SECTION B-B

DETAIL C

DETAIL A

DETAIL C

މICROBIOPSY DEVICE

MICROBIOPSY DEVICE

CROSS-REFERENCE TO RELATED APPLICATIONS

This application is a continuation of co-pending International Patent Application No. PCT/US15/13823 filed Jan. 30, 2015 and claims priority to and the benefit thereof, which application in turn claims priority to and the benefit of then co-pending U.S. provisional patent application Ser. No. 61/934,010, filed Jan. 31, 2014, each of which applications is incorporated herein by reference in its entirety.

FIELD OF THE INVENTION

The invention relates to microbiopsy instruments in general and particularly to microbiopsy devices that employ needle-like structures.

BACKGROUND OF THE INVENTION

Needle biopsy instruments are well known in the medical arts. In spite of progress in disease research, the diagnosis of many diseases, for example cancer, requires that a biopsy be removed from a patient and examined microscopically by a pathologist.

Two general classes of biopsy devices include front-end (or distal end) capture devices and side capture devices. Front-end capture devices tend to be smaller than side capture devices. An example of a front-end device is made by BioPince, and the smallest diameter available for BioPince is a relatively large 18 gauge, requiring a 17 gauge introducer cannula (1400 microns outer diameter).

The smallest and most common front end collection device designs include those currently marketed as Chiba, Westcott, Maxicell, and Procore. All of these are variations on the theme of a tube cut at one acute angle (i.e., beveled once). Such a geometry allows the back part of the bevel to cut the tissue, but only over less than about 50% of the perimeter of the inner bore of the needle.

Chiba-style needles exist in dimensions from larger than 16 gauge to as small as about 31 gauge. For example, 25 gauge needles have a typical ID of 241 microns and an OD of 495 microns, while 27 gauge needles have a typical ID of 190 microns and an OD of 393 microns. Chiba style needles are commonly used for fine needle aspiration (FNA) biopsies in which the intent is to acquire dissociated cells or partially dissociated tissue fragments, but not intact tissue near the size of the ID of the needle.

A discussion of the handling and examination of material acquired using FNA is given in the following U.S. patent documents: Fischer, U.S. Pat. No. 6,913,921, issued Jul. 5, 2005; Fischer, U.S. Pat. No. 7,541,161, issued Jun. 2, 2009; Fischer, U.S. Pat. No. 8,048,669, issued on Nov. 1, 2011; Fischer, U.S. Patent Application Publication No. 2009/0098640, published on Apr. 16, 2009; and Fischer, U.S. Patent Application Publication No. 2012-0040444, published on Feb. 16, 2012, which describe the Cellient™ system.

There are two front end collection devices that are able to effectively cut tissue circumferentially and obtain intact fibrous tissue at a diameter that matches the inner diameter of the device. These are the EZ-EM needle and the three-prong Franseen-type needle. However both these devices reveal a flaw with existing front end collection devices: Existing designs do not sever the tissue at the front end, and thus any tissue procured tends to pull back out of the needle when the needle is withdrawn. EZ-EM needles were designed like a wood boring tool to spin and cut tissue along the cylindrical circle that surrounds the core of procured tissue. Published trials of this needle reported that it did not perform better than other designs, and this has been attributed in part to the failure of the device to sever the tissue at the distal end.

BioPince overcomes this problem specifically by having a sharp blade slide along the outside of the needle, at the front of the tip of the needle, to mechanically sever the core of tissue near the patient. A limitation of this design is that BioPince only cuts one core of tissue for each insertion of the device, thus limiting its usefulness for broad 3 dimensional sampling Two types of Franseen-type tips are known: one is a two prong tip and the other is a three prong tip. The two prong tip is a tube cut at about a 10-15 degree bevel, with a second 10-15 degree bevel cut after rotating the needle 180 degrees. The three-prong Franseen-type tip has three bevels cut at about 10-15 degrees with 120 degrees of rotation between bevels. The Franseen-type design is not available for use in endoscopic ultrasound (EUS) devices or bronchoscopic ultrasound (EBUS) devices. Additionally, Franseen-type needles have not been made from needles smaller than 22 gauge (OD about 700 microns and ID about 400 microns).

Side capture devices generally employ a slot cut into the side of a solid cylinder, near the distal end. The cylinder is advanced into a mass and then a circumferential sharpened guillotine-like sleeve is advanced over the slot to shave off a "core biopsy" which becomes trapped inside the slot. An example of such a core biopsy device is called Tru-cut. ProCore, Maxicell, and Westcott biopsy needles can collect from the single bevel front end (like Chiba) and also from a side capture feature such as a slot cut into a hollow needle near the distal end. The slot provides a cutting surface that scrapes a sample of tissue from the side of the region being examined. A physical limitation of all side capture devices is that device needs to be inserted through the area to be biopsied. This puts a constraint on the use of such instruments since lesions immediately proximal to a vital structure may not be able to be safely biopsied. In addition, tissue that is procured may be distorted from having the distal end of the needle pass through the area to be procured. Another limitation of the core biopsy side capture devices is that most have to be physically removed from the patient, and the tissue physically removed from the slot, before another sample of tissue can be obtained. Thus, side-capture core biopsy devices make it more it more difficult to acquire samples from multiple areas of a mass. To enable the acquisition of multiple pieces of tissue from one area, an introducer tube is frequently used. Such an introducer has an inner diameter that is necessarily a little larger than the outer diameter of the cutting sleeve.

Vacuum-assisted core biopsy devices have been designed to encourage the sample to fall into the slot. Other improvements of the core biopsy device enable multiple fragments to be procured without removing the device from an introducer cannula, but such devices still are unable to collect from more than one area without reintroducing the outer cannula. These improvements are particularly useful for removing contiguous masses of tissue, and they are made in the size range of 14 gauge and larger (millimeters in diameter).

Side-capture core biopsy devices have a certain maximum slot size/geometry that leaves enough material in the solid cylinder to provide mechanical strength to the tip. Together with the need to accommodate an outer cutting sleeve, and accommodation of an outer introducer cannula, side capture core biopsy devices have a relatively low ratio of the diameter of procured tissue to the final outer diameter of the device. The ratio also drops off exponentially as devices become smaller such that the practical lowest size limit for the outer diameter of a side capture device has proven to be about 20 gauge (outer diameter about 1000 microns) in which the ratio of the tissue core diameter to the ratio of the OD falls well below 1:2. In comparison, the ratio of the diameter of the lumen of a front-end collection device and the diameter of the outer wall is more than 1:2 until the device is smaller than about 27 gauge (outer diameter of about 400 microns). Thus, core biopsy devices have intrinsic limitations and are unable to fill the need for wide sampling and procurement of intact tissue fragments in the 200-300 micron range that would otherwise be adequate for diagnosis.

Also known in the prior art is Baylis et al., U.S. Pat. No. 4,099,518, issued Jul. 11, 1978, which is said to disclose an improved biopsy apparatus. The apparatus comprises a hollow outer cannula within which is initially disposed a solid inner puncture trocar. In use, a biopsy sample is obtained from a patient by first inserting the outer cannula—trocar apparatus into the patient to a desired location. Thereafter, the solid inner initial puncture trocar is withdrawn from the outer cannula, while the other cannula remains in place at the desired specimen location. A hollow inner cannula is then inserted into the outer cannula, and upon withdrawal of the inner cannula from the outer cannula the desired specimen is obtained within the hollow interior of the inner cannula.

Also known in the prior art is Fuerst, U.S. Pat. No. 4,651,752, issued Mar. 24, 1987, which is said to disclose a biopsy needle for excising tissue specimens for microscopic examination including a tubular sheath having an axially extending open-side and a tapered point. The open side is provided with opposed grooves which guide a slidable stylet having a tapered end with sharp cutting edges. The tapered end of the stylet is either preformed to curve to the tapered point of the sheath or guided in internal grooves of the sheath to the insertion point of the sheath to occlude the tapered end of the sheath and incise and enclose a tissue specimen.

Also known in the prior art is Rubinstein et al., U.S. Pat. No. 5,885,226, issued Mar. 23, 1999, which is said to disclose a bone marrow biopsy needle provided with blades which cut and retain a biopsy core. In one embodiment, the cutting blades of the needle are hinged at the distal end of the needle and are mechanically coupled to an actuator at the proximal end of the needle. The needle is preferably formed with inner and outer walls to provide a space therebetween for the mechanical coupling. The cutting blades are retained in a dead space against the outer wall of the needle when the needle is open. In lieu of a hinged arrangement, the outer wall of the needle may be tapered at its distal end so that the blades are forced together when they are pushed forward. In another embodiment, the cutting blades are pre-curved inward, but are retained against the inner surface of the needle wall until pushed forward. In yet another embodiment, the distal ends of the cutting blades rest within a curved circumferential recess provided in the needle wall, and, when pushed forward, move together to cut and retain the biopsy core.

Also known in the prior art is Voegele et al., U.S. Pat. No. 6,231,522, issued May 15, 2001, which is said to disclose a surgical biopsy instrument for the extraction of at least one tissue sample from a body having a piercing needle for penetrating the body. The piercing needle has a distal piercing tip and an open proximal end and a passageway extending therebetween. The piercing needle has at least one tissue receiving port adjacent to the piercing tip, and the tissue receiving port communicates with the passageway for the reception of a tissue sample therein. A cutting member is removably disposed within the passageway of the piercing needle and the cutting member has a proximal end and a distal sampling segment. The distal sampling segment has a distal cutting edge and a bore extending therein. The distal sampling segment is moveable across the tissue receiving port of the piercing needle for the cutting of a tissue sample and the tissue sample is received within the bore of the distal sampling segment. The distal sampling segment is breakable from the elongated cutting member.

Also known in the prior art is Eggers et al., U.S. Pat. No. 6,277,083, issued Aug. 21, 2001, which is said to disclose a system, method and apparatus for carrying out the recovery of an intact volume of tissue wherein a delivery cannula distal end is positioned in confronting adjacency with the volume of tissue to be recovered. An expandable metal capture component is expressed from the distal end of the cannula to expand while being electrically excited to electrosurgically cut around and circumscribe the tissue volume. Pursing cables are tensioned to complete the envelopment of the tissue volume, whereupon the volume is recovered by withdrawal of the instrument.

Also known in the prior art is Garcia, U.S. Patent Application Publication No. 2003/0097079, published May 22, 2003, which is said to disclose a sheath for a biopsy needle for removing a sample from a living body, the sheath comprises a substantially tubular structure configured to accommodate at least a portion of a biopsy needle. The tubular structure has a side wall, a first end opening which in use will remain outside of the body, and a second end opening which will in use insert into the body. The tubular portion has a length between the first and second openings which is greater than the distance between sample to be removed and the outside of the body.

Also known in the prior art is McGuckin et al., U.S. Pat. No. 6,425,887, issued Jul. 30, 2002, which is said to disclose a needle assembly comprising an infusion needle that includes a plurality of needle cannulae made of a superelastic material such as nitinol. The needle cannulae are cold-worked or heat annealed to produce preformed bends that can be straightened with in passageway of a coaxial outer cannula for introduction into the body of a patient. Upon deployment from the outer cannula, the needle cannulae substantially return to their preformed configurations for the introduction or extraction of materials at areas lateral to the entry path of the needle assembly. The plurality of needle cannulae can be variably arranged or configured for their distal tip portions to attain a desired infusion pattern such as an umbrella shaped array, and/or be staggered axially.

Also known in the prior art is Pakter et al., U.S. Pat. No. 6,592,559, issued Jul. 15, 2003, which is said to disclose a needle assembly comprising a needle that includes a needle cannula made of a superelastic material such as nitinol. The needle cannula is cold-worked or heat annealed to produce a preformed bend that can be straightened within passageway of a coaxial outer cannula for introduction into the body of a patient. Upon deployment from the outer cannula, the needle cannula substantially returns to the preformed configuration for the introduction or extraction of materials at areas lateral to the entry path of the needle assembly. The needle assembly can comprise a plurality of needle cannulae than can be variably arranged or configured for attaining a desired infusion pattern.

Also known in the prior art is Burbank et al., U.S. Patent Application Publication No. US 2003/0144605, published Jul. 31, 2003, which is said to disclose a device for accessing and for isolating a desired site within a patient's body, and for obtaining a body of tissue from a patient at the site that includes an electrosurgical cutting electrode near the distal tip of a shaft, an anchoring mechanism and an electrosurgical side-cutting device. Methods are provided for accessing a target site within a patient's body, anchoring a body of tissue at the site, and isolating the body of tissue at the site. The method may be performed for a surgical biopsy or lumpectomy at the target site within a patient's body.

Also known in the prior art is Fisher, U.S. Pat. No. 6,709,408, issued Mar. 23, 2004, which is said to disclose a dual action biopsy needle that scrapes tissue of cellular thickness from a lesion during forward and rearward reciprocations of the needle along its longitudinal axis of symmetry. A first sharp edge, formed by a beveled distal end of the needle, scrapes tissue during proximal-to-distal travel of the needle. A second sharp edge is provided by a transversely disposed slot formed in the needle near the first sharp edge. The second sharp edge scrapes tissue during distal-to-proximal travel of the needle. In a first embodiment, the second sharp edge is coincident with an exterior surface of the needle. In a second embodiment, the second sharp edge is elevated with respect to the exterior surface and in a third embodiment the second sharp edge is recessed. Additional embodiments include a second slot, a channel, and a hinge for enabling pivotal movement of the second and third sharp edges.

Also known in the prior art is Balbierz, U.S. Pat. No. 6,770,070, issued Aug. 3, 2004, which is said to disclose a method and apparatus for obtaining a lung biopsy with an apparatus capable of sealing tears within the lung and pleural space to reduce the risk of pneumothorax or pulmonary hemorrhage. The apparatus includes an RF ablation apparatus having a lung biopsy device an energy delivery device including at least one electrode designed to be deployed into target lung tissue, and a sensor. A closure device is operatively coupled to the elongated member to produce an immediate tight seal and promote healing at the tissue interface. A feedback control device is operatively coupled to the sensor and a RF source for controlling energy delivered to the electrodes.

Also known in the prior art is Islam, U.S. Pat. No. 6,890,308, issued May 10, 2005, which is said to disclose a needle for use in taking a bone marrow biopsy comprises a hollow tube having a front end portion formed to a reduced diameter by swaging. The front end is tapered by means of a number of circumferentially-spaced facets, forming a cutting edge. A tapering transition portion, between the main portion of the hollow tube and its reduced-diameter front end portion, is formed with a series of flutes which help in the needle cutting through the cortical bone. A spacer is provided for use in pushing the sample rearwardly out of the hollow tube, the spacer having a through-passage through which a trocar needle is passed and serving for accurate alignment of the distal ends of the hollow tube and trocar needle.

Also known in the prior art is Figueredo et al., International Patent Application Publication No. WO2006/081556, published Aug. 3, 2006, which is said to disclose a biopsy needle includes tissue capture elements within the needle lumen to help hold a tissue sample within the needle and maintain its integrity. According to one aspect, several flexible members form a structure that allows tissue to enter the lumen during advancement of the needle into tissue, and prevents the tissue sample from exiting the needle during retraction of the needle. Examples of the structure include barbs or an etched interior surface of a needle such that the coefficient of friction encountered by tissue differs depending on the direction that the tissue is moving or attempting to move. The flexible members may, in some embodiments, include cutting edges configured to cut the tissue sample from the target tissue mass at the start of needle extraction.

Also known in the prior art is Schembre et al., U.S. Design Pat. No. D657,461, issued Apr. 10, 2012, which is said to disclose the ornamental design for a biopsy needle tip.

Also known in the prior art is Schembre et al., U.S. Patent Application Publication No. 2012/0253228, published Oct. 4, 2012, which is said to disclose a notched tissue-collection needle configured similarly to a fine-needle-aspiration needle is provided with a cutting edge disposed in the notch and configured to excise tissue into the notch for collection. A stylet may be provided through a lumen of the needle during introduction into a patient body. The needle may be provided with echogenicity-enhancing features. The patent application explains that in conventional fine needle aspiration (FNA), a fine needle (e.g., 19-gauge to 25-gauge) is directed to a target site, and suction is applied to the proximal end of a lumen of the needle to aspirate cells through its distal end. The needle is said to include a notch having a central distal lip portion of the distal edge of the notch that preferably forms a proximal-facing cutting edge. The application further explains that current FNA techniques typically obtain only a small number of cells useful for diagnostic evaluation. As a result, this technique includes a risk of false negatives where the few cells obtained in a sample do not accurately represent the presence of a tumor or other disease condition. The small sample size may also limit the diagnostic value of the procedure if the cells obtained are sufficiently few in number or sufficiently damaged during collection that they do not enable a definitive diagnosis. The use of the disclosed device is said to involve a user quickly retracting a cannula proximally such that the proximal-facing cutting edge of the distal notch's central lip cuts a sample of tissue from the target site that is drawn into the lumen and that may be captured within, distal, or proximal of the notch.

Also known in the prior art is Koehler, U.S. Pat. No. 8,388,550, issued Mar. 5, 2013, which is said to disclose a guidable cutting instrument for cutting a tissue specimen from a tissue mass comprises a cannula having a curve formed along a distal portion thereof, and a stylet having a specimen-receiving notch and a curve formed along a distal portion thereof. The stylet is received in the cannula, and is axially extendable therefrom such that the notch is capable of penetrating the tissue mass. The cannula is axially movable over the extended stylet for severing the specimen from the mass for capture in the notch. The cannula and stylet are each structured and arranged for relative rotation between a first position wherein the cannula curve and the stylet curve are in phase to define a curved condition for a length of the cutting instrument, and a second position wherein the cannula curve or stylet curve is rotated relative to the other curve in a manner to define a generally linear condition of the cutting instrument. The selective relative curvature allows the cutting instrument to be steered around obstructions encountered in the body under real time visualization.

The previously described inventions all have shortcomings related to one or more of the following: their large size compared to a useable biopsy sample in the range of less than about 300 microns in diameter; the inability to capture fragments at the front end, thereby avoiding damage to more distal structures or damage to the tissue being biopsied; the inability to continuously capture tissue fragments with one insertion of the device, thus limiting the ability for three dimensional sampling; and avoidance of crushing of a biopsy sample due to clogging of the receiving part of the biopsy device.

There is a need for improved biopsy systems and methods that can provide biopsy samples that have sufficient intact tissue for diagnosis.

SUMMARY OF THE INVENTION

According to one aspect, the invention features a microbiopsy needle tip. The microbiopsy needle tip comprises a tubular elongate structure having a proximal end and a distal end, the distal end having an outer diameter OD and defining an aperture having a circular cross section centered on a central axis of the tubular elongate structure, the aperture having an inner diameter $ID_1$ at the distal end; the distal end having at least three sharpened points projecting axially therefrom and having at least three points of attachment to the tubular elongate structure where pairs of the at least three sharpened points meet, the at least three sharpened points confined dimensionally within an annulus defined by the outer diameter OD and the inner diameter $ID_1$, the at least three sharpened points defining cutting surfaces, the cutting surfaces joining at the at least three points of attachment to the tubular elongate structure, the tubular elongate structure having a distal collection portion with diameter $ID_1$; the tubular elongate structure having a step-out at a location nearer the proximal end than the at least three points of attachment of the at least three sharpened points, the inner diameter of the tubular elongate structure being increased from $ID_1$ to an inner diameter $ID_2$ for a distance along the central axis in a proximal direction so as to define a proximal collection portion having the inner diameter $ID_2$, such that $ID_2$ is larger than $ID_1$; the microbiopsy needle tip having the property that a biopsy specimen of intact tissue having a diameter substantially equal to $ID_1$ can be procured and can be retained within the proximal collection portion for later recovery.

In one embodiment, the outer diameter OD is the diameter of a 22 gauge needle.

In one embodiment, the outer diameter OD is the diameter of a 23 gauge needle.

In one embodiment, the outer diameter OD is the diameter of a 25 gauge needle.

In another embodiment, the outer diameter OD is the diameter of a 27 gauge needle.

In yet another embodiment, the outer diameter OD is in the range from the outer diameter of a 22 gauge needle to a 27 gauge needle.

In yet another embodiment, the proximal collection portion extends along the central axis for sufficient length to contain a plurality of biopsy specimens of intact tissue each having a diameter substantially equal to $ID_1$.

In still another embodiment, the proximal collection portion diameter $ID_2$ is small enough to retain the plurality of biopsy specimens of intact tissue each having a diameter substantially equal to $ID_1$ in the order in which the plurality of biopsy specimens are procured.

In a further embodiment, the tubular elongate structure has an aperture that extends along the central axis of the tubular elongate structure from the proximal end to the distal end.

According to another aspect, the invention relates to a microbiopsy needle. The microbiopsy needle comprises a hollow needle having a proximal end and a distal end, wherein the improvement comprises a microbiopsy needle tip attached to the distal end of the hollow needle, the microbiopsy needle tip comprising a tubular elongate structure having a proximal end and a distal end, the distal end having an outer diameter OD and defining an aperture having a circular cross section centered on a central axis of the tubular elongate structure, the aperture having an inner diameter $ID_1$ at the distal end; the distal end having at least three sharpened points projecting axially therefore and having at least three points of attachment to the tubular elongate structure where pairs of the at least three sharpened points meet, the at least three sharpened points confined dimensionally within an annulus defined by the outer diameter OD and the inner diameter $ID_1$, the at least three sharpened points defining cutting surfaces, the cutting surfaces joining at the at least three points of attachment to the tubular elongate structure, the tubular elongate structure having a distal collection portion with diameter $ID_1$; the tubular elongate structure having a step-out at a location nearer the proximal end than the at least three points of attachment of the at least three sharpened points, the inner diameter of the tubular elongate structure being increased from $ID_1$ to an inner diameter $ID_2$ for a distance along the central axis in a proximal direction so as to define a proximal collection portion having the inner diameter $ID_2$, such that $ID_2$ is larger than $ID_1$; the microbiopsy needle tip having the property that a biopsy specimen of intact tissue having a diameter substantially equal to $ID_1$ can be procured and can be retained within the proximal collection portion for later recovery.

In one embodiment, the outer diameter OD is the diameter of a 22 gauge needle.

In one embodiment, the outer diameter OD is the diameter of a 23 gauge needle.

In one embodiment, the outer diameter OD is the diameter of a 25 gauge needle.

In another embodiment, the outer diameter OD is the diameter of a 27 gauge needle.

In yet another embodiment, the outer diameter OD is in the range from the outer diameter of a 22 gauge needle to a 27 gauge needle.

In yet another embodiment, the proximal collection portion extends along the central axis for sufficient length to contain a plurality of biopsy specimens of intact tissue each having a diameter substantially equal to $ID_1$.

In still another embodiment, the proximal collection portion diameter $ID_2$ is small enough to retain the plurality of biopsy specimens of intact tissue each having a diameter substantially equal to $ID_1$ in the order in which the plurality of biopsy specimens are procured.

In a further embodiment, the tubular elongate structure has an aperture that extends along the central axis of the tubular elongate structure from the proximal end to the distal end.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

In the drawings, the following numerals are used to identify specific parts:

Figure 5A:
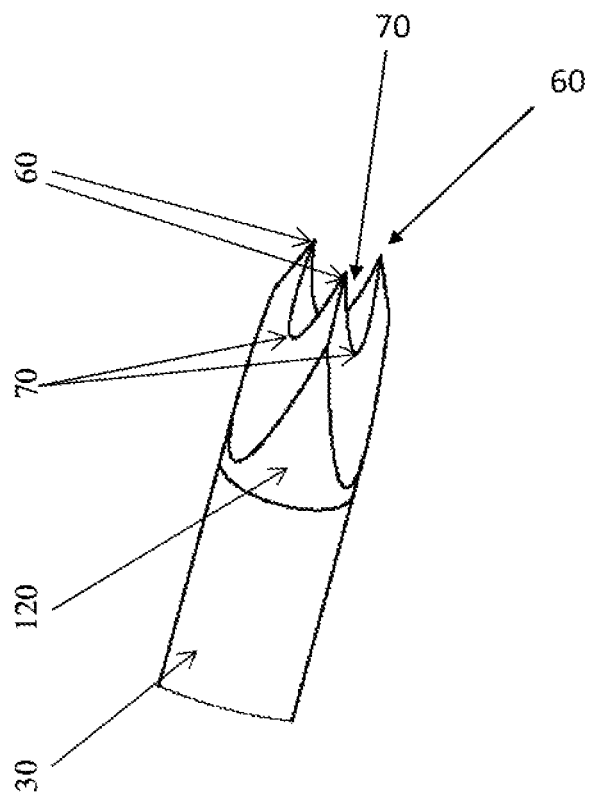
Figure 5B:
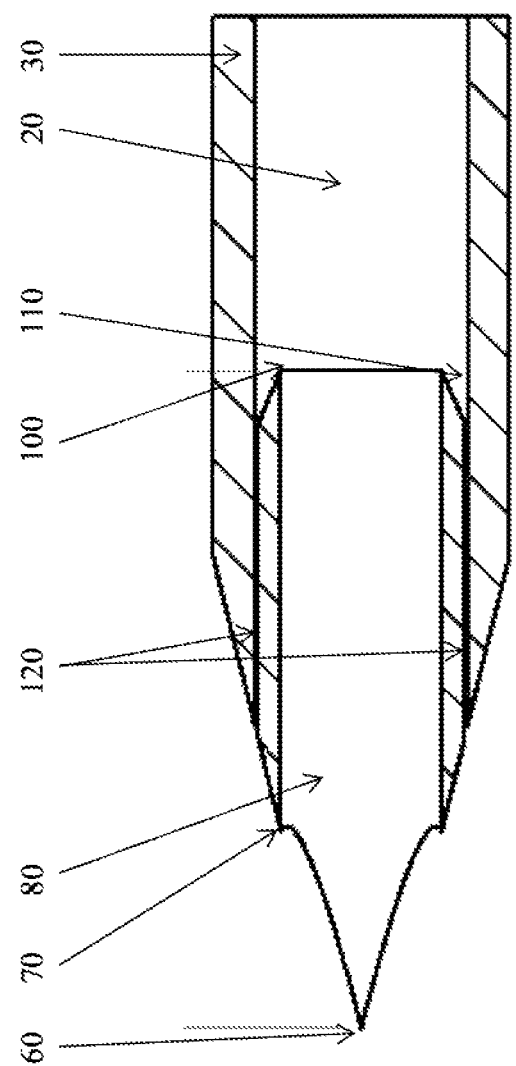
Figure 5C:
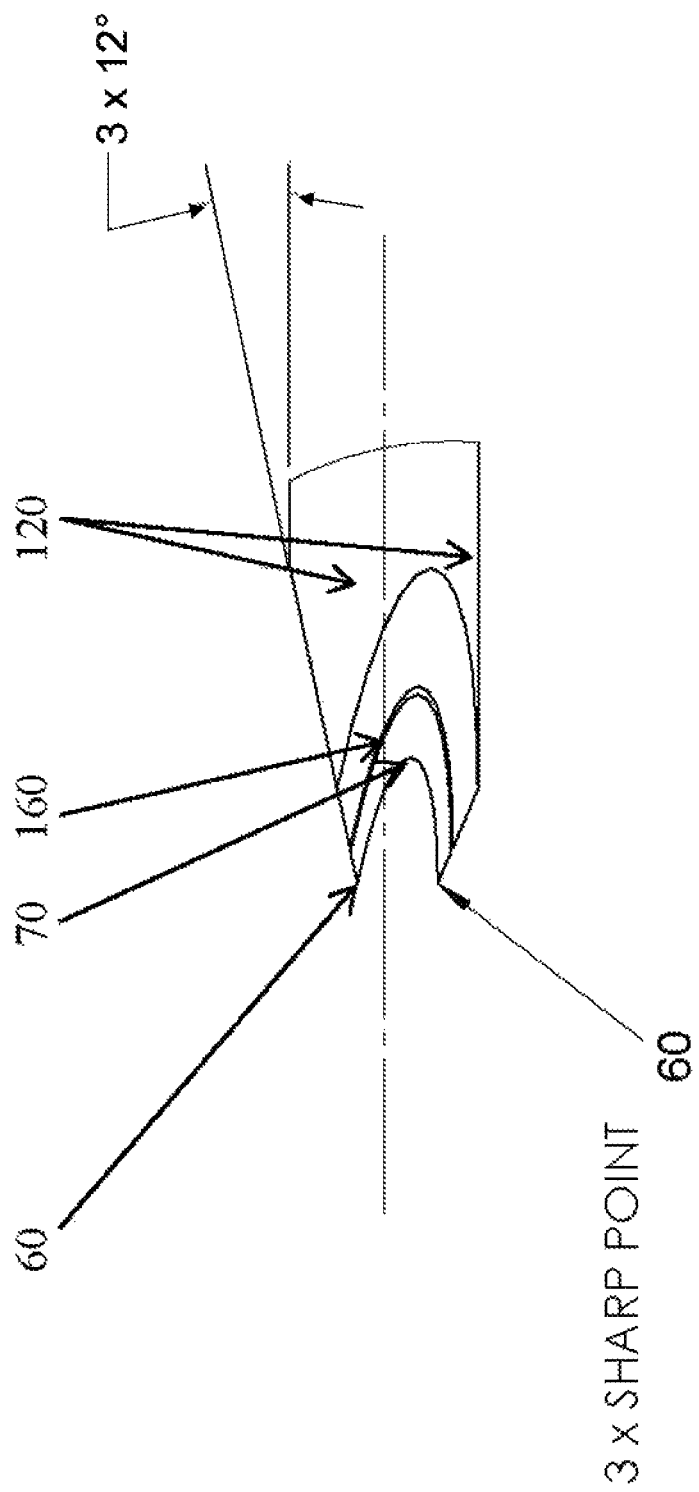
Figure 8:
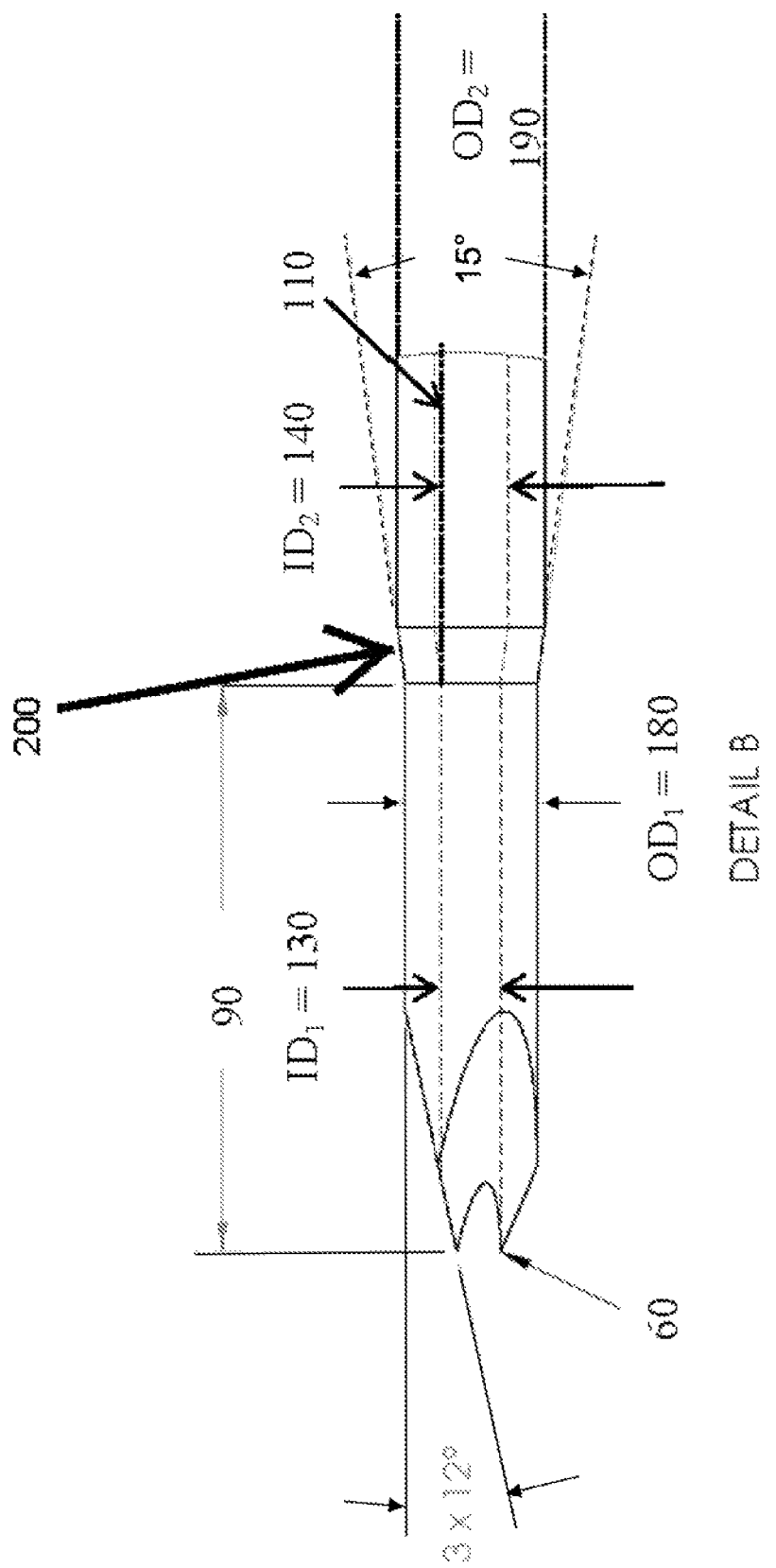

10 Distal end of device
20 Proximal collection portion of the device
30 Hollow needle encompassing of the proximal collection portion of device
40 Luer-lock-type fitting at the proximal end of needle
50 Water tight seal between 30 and 40
60 Distal-most end of cutting surface
70 Proximal part of cutting surface
80 Distal collection chamber
90 The length of the distal collection chamber
100 Proximal-facing bevel tip or back-facing barb
110 Step out (difference between distal inner diameter and the proximal inner diameter
120 Points at which laser welding can bond two hollow needles to allow formation of a step-out.
130 Inner diameter of the distal collection chamber
140 Inner diameter of the proximal collection portion of the device
150 Outer diameter of the proximal collection portion of the device
160 Junction between the two hollow tubes that can be combined to make the device according to the embodiment of FIG. 5C.
170 The 10-15 degree bevel of distal end of device
180 Outer diameter of the distal end of the device according to the embodiment of FIG. 8.
190 Outer diameter of the proximal collecting portion of the device according to the embodiment of FIG. 8.
200 The 10-20 degree angle created by swaging near the distal end of the hollow needle.
210 Swaged segment proximal to the distal tip.

Figure 1:
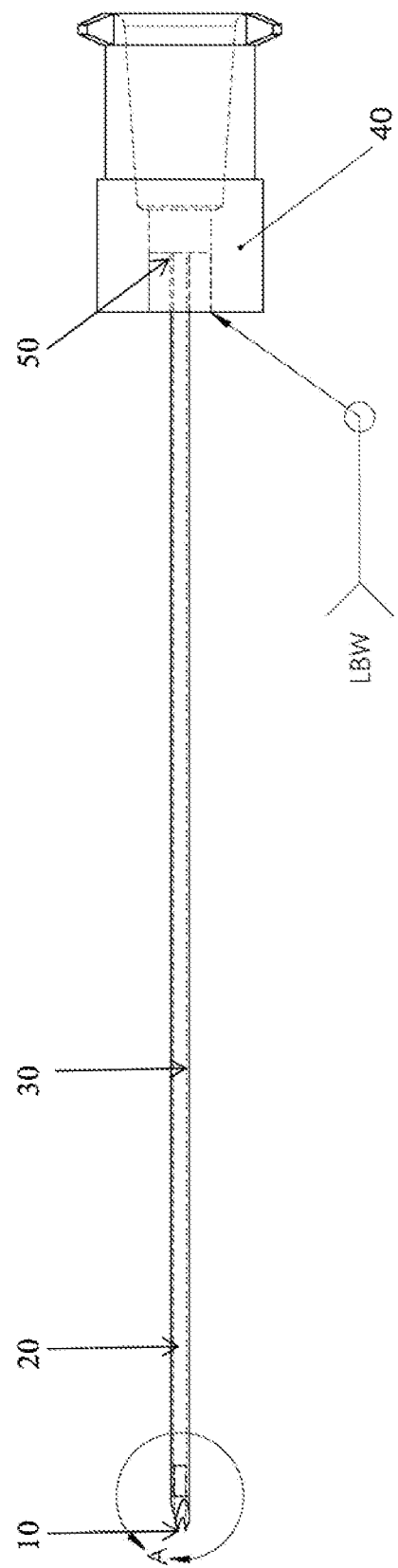

FIG. 1 is a diagram in side view of a first embodiment of a biopsy needle having a distal tip and a proximal hub with a Luer-lock connector for attachment to a syringe according to principles of the invention.

Figure 2A:
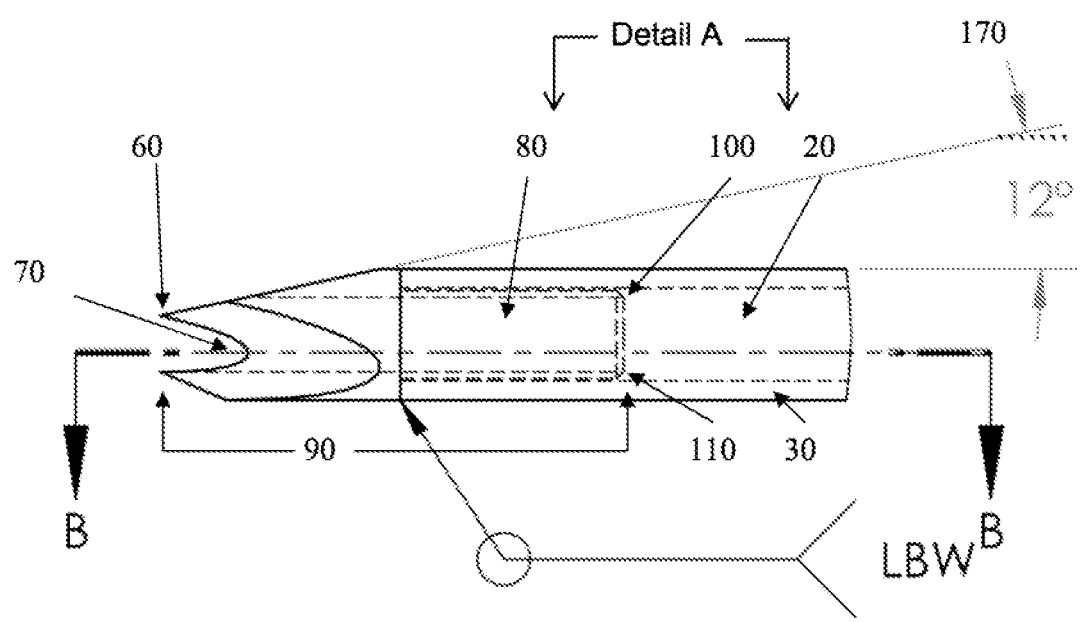

FIG. 2A is a diagram in side view of one embodiment of a distal tip of the biopsy needle of FIG. 1 according to principles of the invention.

Figure 2B:
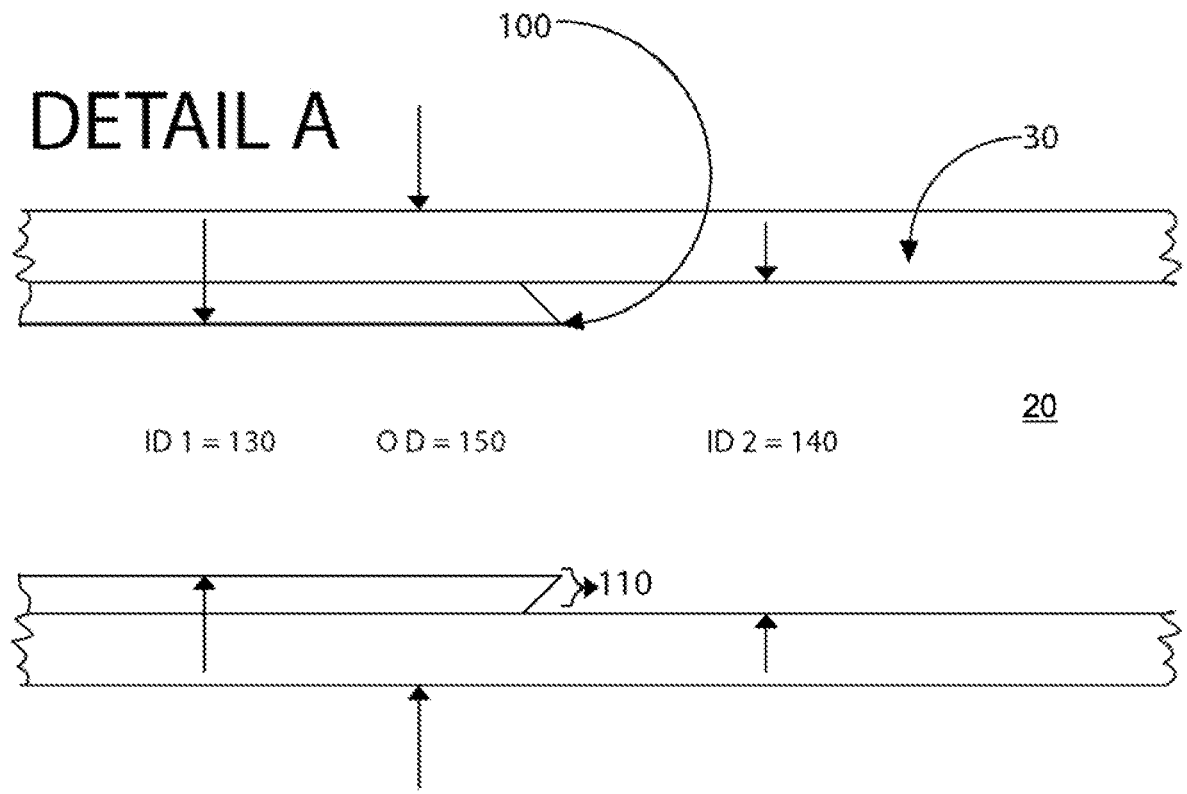

FIG. 2B (Detail A) is a diagram in cross section of one embodiment of a distal tip of the biopsy needle of FIG. 1 that shows backwardly facing barbs according to principles of the invention.

Figure 3:
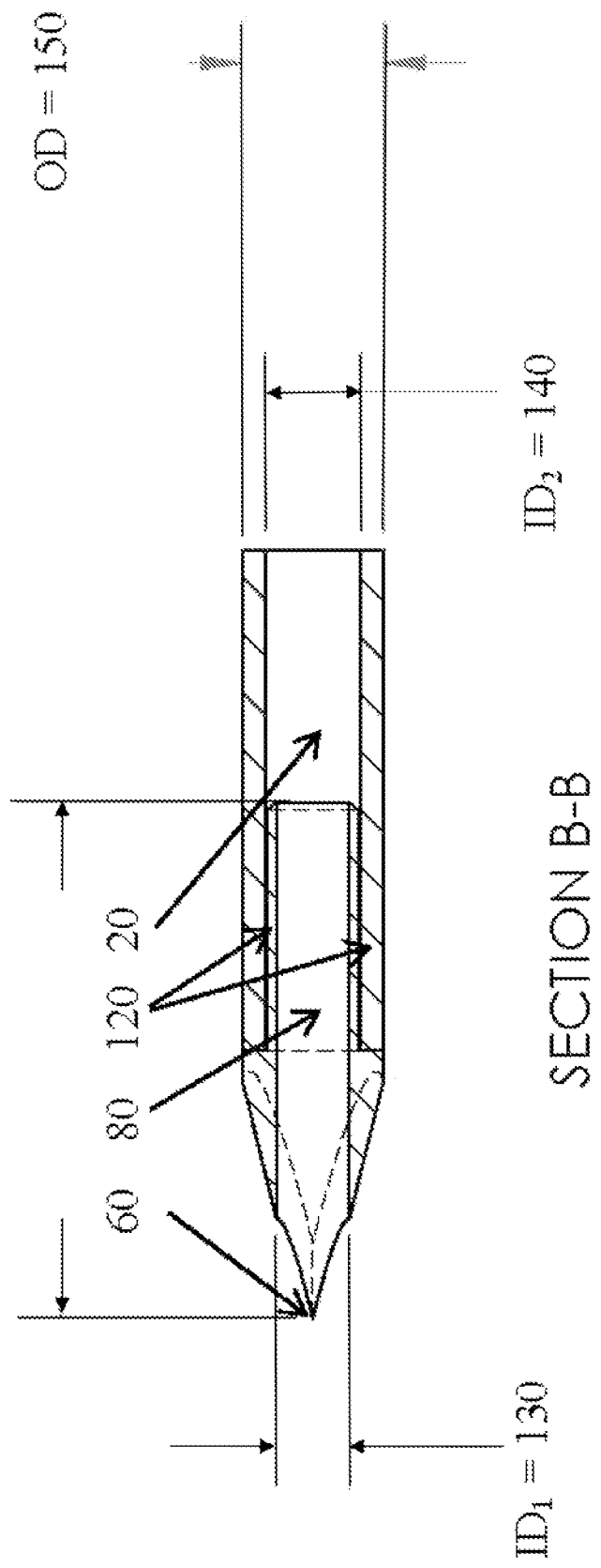

FIG. 3 is a diagram in cross section of the distal tip of FIG. 2A according to principles of the invention.

Figure 4:
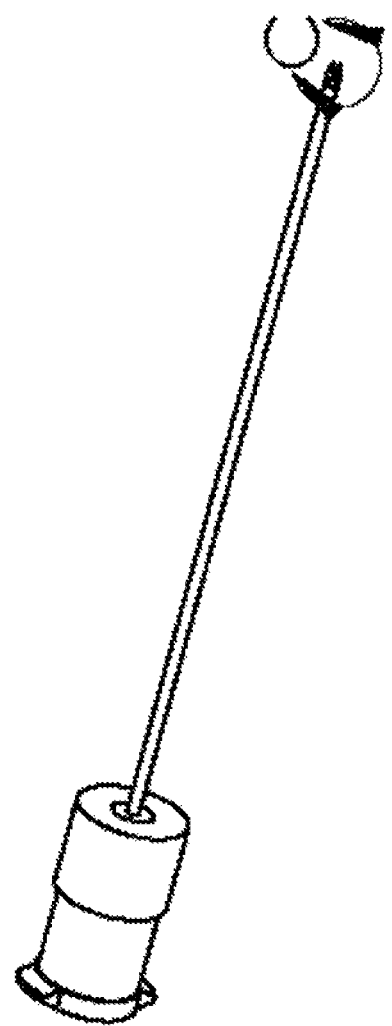

FIG. 4 is a diagram in perspective view of the first embodiment of a biopsy needle having a distal tip according to principles of the invention.

FIG. 5A is a diagram in perspective view of the distal tip of the biopsy needle of FIG. 4 according to principles of the invention.

FIG. 5B is a diagram in cross-section of another embodiment of a distal tip showing a different method for manufacturing the step-out and back-facing bevel using two pieces of tubing that insert into each other, with the proximal tube having an inner diameter that matches the outer diameter of a more distal tube, according to principles of the invention.

FIG. 5C is a diagram in perspective view of the distal tip of the biopsy needle according to the embodiment of FIG. 5B.

Figure 6:
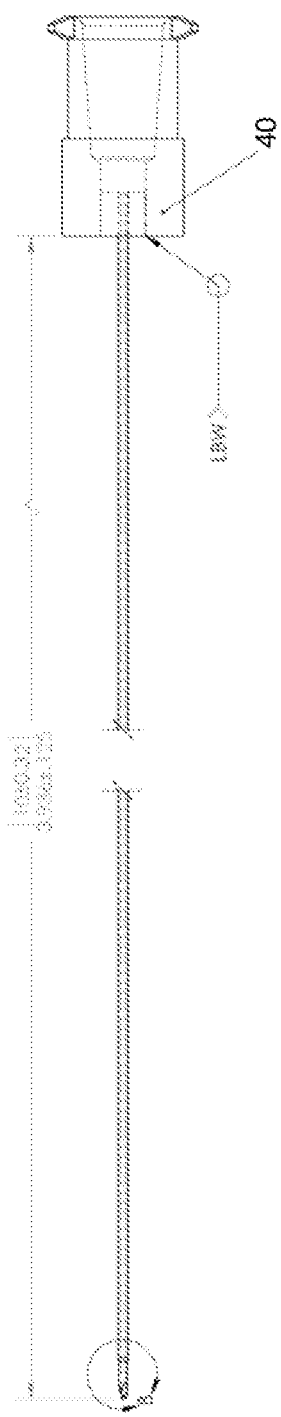

FIG. 6 is a diagram in side view of a another embodiment of a biopsy needle having a distal tip in which the distal tip of the needle has been swaged down to effect a step-out in the inner diameter, according to principles of the invention.

Figure 7:
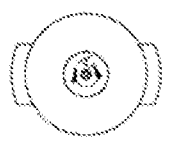

FIG. 7 is a diagram in end view of the second embodiment of a biopsy needle having a distal tip according to principles of the invention.

FIG. 8 is a diagram in side view of the distal tip of the biopsy needle of FIG. 6 according to principles of the invention. The tip illustrated in FIG. 8 includes a step-out.

Figure 9:
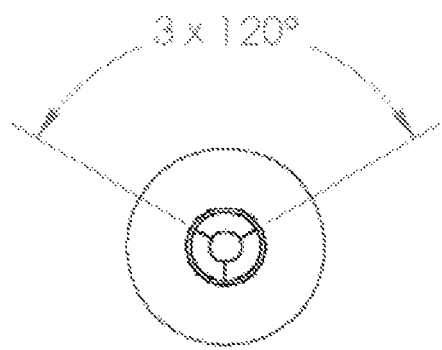

FIG. 9 is a diagram in end view of the distal tip of the biopsy needle of FIG. 6 according to principles of the invention.

Figure 10:
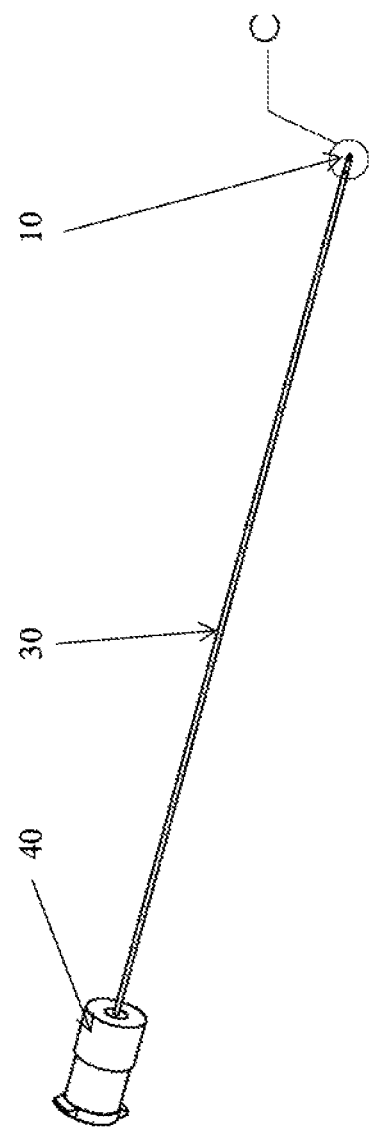

FIG. 10 is a diagram in perspective view of the biopsy needle of FIG. 6 according to principles of the invention.

Figure 11:
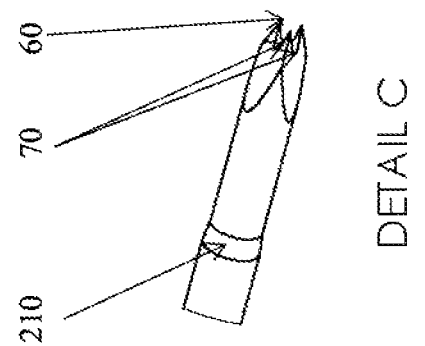

FIG. 11 is a diagram in perspective view of the distal tip of the biopsy needle of FIG. 6 according to principles of the invention.

DETAILED DESCRIPTION

As used herein, the term "proximal" refers to the end of a device that when in use is held by a user or to the end of an elongate device that is nearest a user when in use, and the term "distal" refers to the end of the device that contacts the tissue to be sampled.

As used herein, the term "intact tissue" means a tissue fragment that is not crushed or scrambled, e.g., one in which the cells present are in substantially the same relative arrangement as they are in situ.

As used herein, the term "distal cutting tip" means a cutting tip located at the distal end of a biopsy needle.

As used herein, the term "distal collection portion" means a collection portion or region located at the distal end of a biopsy needle.

As used herein, the term "proximal collection portion" means a collection portion or region located at a distance from the distal end of a biopsy needle toward the proximal end of a biopsy needle.

As used herein, the term "step-out" used as a noun means an increase in the circular diameter of a needle as one moves from the distal toward the proximal end of the device. In moving in the opposite direction, the inner diameter of the needle is reduced.

As used herein, the term "hub" means the proximal-most portion of the biopsy device. A hub can allow the biopsy device to make a water tight seal with a syringe, for example via a Luer-lock connection.

As used herein, the term "needle curvature" means a deviation from an otherwise straight alignment of the biopsy needle.

Front end collection devices are preferable to side-capture core biopsy devices for several reasons: First, they can be manufactured at a generally smaller diameter, and the ratio of the diameter of the device to the diameter of tissue procured can be more favorable. Second, front end collection devices allow sampling in front of vital structures that otherwise risk being cut by the distal tip of core biopsy devices. Third, front end collection devices can allow sampling in three dimensions in one single needle insertion. However, existing front-end collection devices are known to have a number of limitations. A first limitation of front end collection devices is that most designs do not cut tissue circumferentially. Another limitation with existing front end collection devices is a result of the fact that they do not sever the tissue at the distal end, and thus any tissue procured tends to pull back out of the needle when the needle is withdrawn.

Still another limitation of some devices is that the device has to be removed from the patient and the tissue removed from the device each time a sample from one specific location is obtained. Still another limitation of other front-end collection devices cannot collect multiple samples in one needle insertion without crushing the samples.

In order for tissue to be severed if not simply cut by a blade in a front-end collection device, planes must develop within in the tissue to be sampled that allow the tissue to rip across the full diameter of the sample, which is preferably equal to the diameter of the inner bore of the device. I have discovered that in some instances there are natural planes of separation for tissues to fracture. Many natural planes of separation exist in some tissues, such as liver, normal pancreas, and normal salivary gland, enabling Chiba-style devices to acquire fair amounts of such tissue even when they cannot cut circumferentially. However, I have directly observed that tissue fragments acquired from these sites using Chiba and related biopsy needles are usually not the full diameter of the inner bore of the needle. The recovered fragments are also short in length, generally much less than 1 mm, in spite of mechanical motions that should in principle be able to acquire tissue fragments centimeters in length. Shortness may be due to the need for the device to exert pressure perpendicular to the axis of the needle for the single bevel to engage the tissue. Finally, Chiba-style needles tend to crush tissue samples.

Importantly, fibrous tissue is procured very poorly with all of the available Chiba-style and related devices. Virtually all fibrous tissue fragments that can be procured with such front end devices show some crush; it seems likely that the crushing has to do with the tissue occasionally becoming bunched up into the needle tip to the point where the bunch of tissue has more mechanical strength than adjacent tissue planes, planes that then eventually rip. This limitation is significant since pathological tissue often has a component of scarring (fibrous tissue). For example, autoimmune pancreatitis is characterized by scarring, and many invasive carcinomas (the most common group of cancers) typically have scarring ("desmoplasia") associated with the cancer cells. Generally, any of the side capture devices and the Biopince front end capture device are all able to acquire intact fibrous tissue fragments. Scar tissue is three-dimensionally cross-linked, and the lack of tissue planes that can easily split appears to account for the difficulty of existing front-end capture devices to collect intact fibrous tissue.

Through direct experimentation using uterine fibroids, such as leiomyomas, a kind of tumor that is three-dimensionally cross-linked and emulates the most difficult type of tissue to biopsy, I have found that Franseen-type needles procure a core of tissue from such tissues whose diameter matches the inner diameter of the bore of the needle. However, tissue procured can be seen (with the aid of a dissecting microscope) to slip out of the distal end of the Franseen needle as it is being withdrawn.

Improvements in diagnostic techniques, such as molecular and immunohistochemical tests, and improved diagnostic criteria (A. H. Fischer et al., The Cytologic Criteria of Malignancy, Journal of Cellular Biochemistry 110:795-811 (2010)) have decreased the amount of tissue that is required for diagnosis. There have also been improvements in the efficiency of biopsy processing, e.g., through the introduction of Cellient™ that automates processing and eliminates chance for cross contamination. Cellient™ allows diagnostic biopsy fragments that are too small to be physically held with forceps to be efficiently recovered at an indexible plane in paraffin for paraffin-embedded sectioning. The minimal size of a biopsy is usually defined by a requirement for certain tissue-architectural information, rather than the number of cells needed for immunohistochemistry or molecular-based testing. The amount of tissue architectural information depends on the particular diagnosis.

As a general guideline for development of an optimal biopsy device, for the vast majority of human cancers diagnostic large-scale tissue architectural features span a diameter of only about 200-300 microns (S. Istvanic, et al., Cell Blocks of Breast FNAs Frequently Allow Diagnosis of Invasion or Histological Classification of Proliferative Changes, Diagnostic Cytopathology, Vol 35, No 5, 263-269, Wiley, 2007; Weaver V M, Fischer A H, Peterson O W, Bissell M J. The importance of the microenvironment in breast cancer progression: recapitulation of mammary tumorigenesis using a unique human mammary epithelial cell model and a three-dimensional culture assay. *Biochemistry Cell Biology*. 1996; 74 (6):833-51). For example, the determination of whether or not a lump is a breast cancer requires perhaps a few hundred cells, in clusters of roughly 20-50 microns in diameter. However to determine whether the breast cancer is invasive or still growing in a non-life-threatening in situ manner requires fragments of intact tissue 200-300 microns in diameter. Multiple samples taken from a number of locations in and around a tumor are very helpful in defining the type of tumor and predicting its behavior, thereby allowing treatments to be optimized.

I believe that unanticipated scaling effects, which are further described below, will allow a needle having an inner diameter smaller than that of a 22 gauge Franseen-type tip (and possibly smaller gauge, such as 27 gauge) to have great utility for microbiopsy procurement, especially when coupled with other features in this invention.

The Franseen-type needle design is a triple beveled hollow tube, with each bevel about 12 degrees. The resulting shape spreads the stress on the tissue radially away from the core of tissue that is procured. In comparison, a circumferential conical bevel (e.g., like the tip of a sharpened pencil) can be directly observed to act like a wedge that splits the tissue linearly across the central core, and prevents a core from being procured. In experiments with cross-linked tissues, conical-shaped device tips allow procurement of less than a mm of tissue. When a conical-shaped tip is inserted into the tissue, there is great resistance for about the length of tissue that is procured (<1 mm) then suddenly resistance to needle insertion decreases. I inferred that the conical shape acts like a wedge to induce a micro planar fracture in the tissue, and proved this histologically by studying the tissue that was biopsied. The planar fracture is analogous to the split that develops when pounding a thick nail into soft wood. Once a tissue fracture develops, the device cannot effectively re-enter the tissue to procure additional tissue. It is the thickness of the wall of the biopsy device that exerts pressure on the tissue that leads to such a split, and front-end collection devices appear to offer the minimal size of the wall of the biopsy device. Planar fractures appear to propagate for perhaps millimeters distal to the tip, ultimately causing a conical device to fall into a fracture and stop collecting tissue.

When a Franseen-type needle is inserted into tissue, the tissue first "sees" three sharpened points that are at the outer edge of the circular profile of tissue that will be actually procured. As the Franseen tip is inserted further, the three points become three triangular shapes, with an acute angle pointing perpendicular to the core of tissue that will be procured and the base of the triangle defining the perimeter of the core being procured. As the Franseen-type tip is advanced, there is no force exerted that can propagate into the core. All forces exerted on the tissue by virtue of the space-occupying wall thickness of the device are presented to the tissue as three splitting forces outside and perpendicular to the core of procured tissue. As the tips advance, the inner portion of the tips prevents the split from propagating into the core of tissue. As the core advances, three sharp cutting surfaces at the base of the three tips make a clean circular cut. Three-way splits emanating away from the procured core can be seen when the biopsied tissue is examined histologically. The effectiveness of this needle design was also demonstrated in large scale models that I have constructed, which have been used to cut various materials such as cloth, and closed-cell extruded polystyrene foam (Styrofoam™).

There are three problems with the existing Franseen-type needle, however. First, it is only available in 22 gauge designs. It should be highly effective at procuring diagnostic tissue fragments if it were made at smaller diameters. Second, there is no step-out to the inner diameter of the needle in any existing design. Without a step-out, only a limited amount of tissue can enter the needle before it clogs. As the friction builds up in the needle, tissue that continues to be procured tends to become crushed. Third, there is no barb directed toward the proximal portion (backward facing barb) of the Franseen-type needle. Backward facing elements could help to hold the tissue within the needle when the needle is withdrawn.

In experiments with prototypes manufactured for me according to my specifications, some of which are illustrated in the drawings, I have documented advantages over the existing microbiopsy device available for endoscopy. For example, a 22 gauge device with a Franseen-type tip, a step-out, and a back-facing barb illustrated in FIG. 1 through FIG. 4 outperforms the commercially available endoscopic ultrasound (EUS) and endoscopic bronchoscope ultrasound (EBUS) fine needle biopsy devices. The prototype shown in FIG. 1 through FIG. 4, manufactured with a distal collection diameter and an outer diameter of a 22 gauge needle outperforms a 22 gauge Chiba-style needle and the 22 gauge ProCore™ needle in terms of the length of tissue procured per 1 cm forward thrust of the needle, the percentage of successful procurements of tissue per thrust and withdrawal cycle, and the total amount of intact tissue. Franseen-type tips are not available for EUS and EBUS needles. However, the prototype illustrated in FIG. 1 through FIG. 4 with a step-out and back-facing barb outperform an otherwise identical 22 gauge Franseen needle lacking a step out and back-facing barb in terms of the total amount of tissue that can be continuously collected without emptying the proximal collection chamber and the average lengths of the cores when multiple cycles of insertion and withdrawal are performed.

Through experience with varying diameter devices, I have appreciated unexpected scaling factors that operate in favor of smaller-sized devices. For example, smaller diameter Chiba needles appear paradoxically to procure a larger amount of tissues such as thyroid when compared to larger diameter Chiba needles. This is likely to be due to the requirement for a Chiba needle to rip the tissue at a plane across the diameter of the needle; such completely traversing planes being unlikely if the diameter is larger. For more cross-linked tissues, the tensile strength is likely to be relatively high and uniform for any large diameter core of tissue that could be obtained with a circumferential front cutting edge. The tensile strength of tissue decreases with the square of the diameter, implying that tissue will be able to spontaneously rupture and be retained within the needle when a smaller core of tissue has been procured. Furthermore, as the device is scaled down, natural inhomogeneities in the tissue (for example capillaries that present areas devoid of tensile strength) are predicted based on my observations to expose planes of cleavage that can allow small cores of tissue to break away from the tissue being sampled and be retained within the needle. Experimentally these unanticipated scaling effects were proven. A 22 gauge Franseen type needle (without a step-out) cannot retain a fragment of a procured leiomyoma when the needle is slowly retracted (the core of tissue is observed to slip out of the distal part of the needle). With a 24 gauge or smaller Franseen tip (without a step-out), a procured core of leiomyoma is retained within the tip using the same dynamics for insertion and withdrawal of the device. Thus a back-facing barb and a smaller diameter have complementary effects at retaining tissue cores obtained with efficient Franseen needle tips.

In addition to being generally smaller, front-end capture devices should generally enable multiple collections of biopsy fragments as a needle is advanced into different areas. Continuous collection theoretically enables excellent sampling because multiple portions of a mass can be procured in one "pass" by repeatedly pulling back and re-directing the needle forward, without having to ever completely remove the needle.

One of the obstacles to continuous collection is that the most functional existing front end collection devices ultimately become packed with tissue fragments which impede the entry of additional fragments and/or cause any additional fragments to lose their intactness, making them unusable for diagnosis. This occurs at approximately 10 mm for liver tissue procured with a 22 gauge Franseen needle. I directly observed that preloading a Franseen-type needle with a 10 mm core of fibrous tissue causes the needle to crush and distort soft lymphoid tissue if the fibrous core is present in the Franseen needle. Crushing and distortion of lymphoid tissue does not occur if the lymphoid tissue is collected with an empty Franseen needle. Thus, jamming of the inner bore of existing Franseen needles limits their usefulness for procuring a wide sample, especially for delicate tissues (such as lymphoid tissue).

A step-out of the inner diameter of the proximal collection portion of the device has the unanticipated effect of enabling continuous wide sampling. In direct experiments, I can demonstrate that the maximum length of tissue fragments that can be jammed without distortion into a 22 gauge Franseen needle is roughly 10 mm when there is no step-out. For the 22 gauge prototype shown in FIG. 1 through FIG. 4, the amount of tissue (ex vivo) that can be continuously collected appears unlimited (tissue eventually extrudes from the hub of a 5 cm needle).

The improved performance of the present microbiopsy needle in various embodiments is attributable to the presence of one or more combinations of features. These include the use of a Franseen-type needle cutting tip; the provision of a "step-out" in which the collection portion of the biopsy device has a larger diameter than the procuring portion of the device, the step-out provided to allow tissue cores to be continuously procured and flow unimpeded by friction into the proximal barrel (or a proximal collection portion) of the needle; frictional force on the core of tissue exerted by the distal portion of the needle, which force is provided by the diameter of the distal collection portion of the device having substantially the same diameter as that of the procured core of tissue; the mechanical effects of scaling the needle to small dimensions; and the contemplated use of a needle that can be curved to as to sample multiple biopsy sites in close proximity without retracting the needle from the patient. The curved operation, or needle curvature, can be used to direct the needle to sample a plurality of different adjacent sites without having to extract the needle from the patient and reintroduce the needle to procure successive biopsy specimens.

A variety of manufacturing methods can make the biopsy needle. For example, in FIGS. 1-5A, a step-out and a back-facing barb can be manufactured by machining a lap-joint between two tubes with identical outer diameter and differing inner diameters. Laser welding can be used to assure a stable union. Alternatively, as shown in FIGS. 5B and 5C, the same geometry of the step-out and back-facing barb can be achieved by inserting one tube with a tight fit into another tube, followed by laser welding. It is feasible to manufacture the device with a step-out generated by swaging (compressing) the outer diameter of the distal end of the tube before grinding a Franseen-type tip. The swaging reduces the inner diameter, thereby generating a step out. Other methods of manufacturing can also be envisioned by one of ordinary skill in the field.

In addition, it is believed that the method of use of the disclosed biopsy needle is novel. Through direct observation, it is apparent that cross-linked tissue that has entered the distal collection chamber can slip out of the chamber if the biopsy device is withdrawn slowly. Tissues appear to have sufficient elasticity to allow them to delay the exit from the needle. Through experimentation, I have found that if the needle is quickly withdrawn and then immediately reinserted (preferably at a slightly different angle, for example by slightly rotating a slightly curved needle as it is being withdrawn), the biopsy device will cut back across the core and sever it from its connection to the surrounding tissue. The speed at which elastic tissue slips out of the needle appears to be slower for thinner diameter Franseen needles, an unanticipated scaling effect that favors smaller diameter devices. Thus, the diameter of the needle, the means of introducing the needle, withdrawing it, rotating it, and re-introducing the needle are important and overlooked aspects of the function of a microbiopsy device.

The length of the distal collecting chamber (90) is an important variable. If the chamber is too long (for example longer than about 5 mm for a 22 gauge needle with an inner diameter of 400 microns), then tissue will be impeded from entering the device, or any procured tissue will lose its intactness. If the distal collection chamber is too short, insufficient friction will develop to impede a distally directed exit of the core of tissue before the device can be reinserted to cut back across the core and capture it, unless a backfacing barb is incorporated. The frictional force in the distal collection portion can be measured experimentally by loading a core of tissue of different lengths into Franseen needle (e.g., by piercing through a slab of tissue to assure its capture) and then measuring the pressure on a syringe that is required to dislodge the core. Experimentally, one atmosphere of pressure (13 pounds per square inch) is the static friction exerted by 6 mm of leiomyoma on a 22 gauge needle (400 microns diameter). From such measurements and the foregoing considerations, it is likely that for an embodiment of this invention with an inner diameter of the distal collection chamber (110) equal to about 250 microns, the optimal length of the distal collection chamber (90) would be less than 10 mm and possibly between 1 and 4 mm. A back-facing barb (100) should diminish the optimal length of the distal collection chamber.

It is contemplated that an automated system can be produced that is capable of causing a biopsy needle to be correctly operated according to the principles of the present invention. Such an automated system would have the benefit for the patient that the biopsy procedure could be accomplished correctly the first time and in a short duration of time, because the automated system would be designed to operate repeatably and as quickly as reasonably possible, as compared to the operation of a manual system which is subject to procedural variation depending on the experience and skill of the operator. Such an automated system would have the cost benefit that a person who is not experienced in performing needle biopsies will be able to perform such a biopsy by employing the automated system, so that the expense of performing the procedure can be controlled.

It is contemplated that an automated system can be produced that is capable of causing a biopsy needle to be correctly operated to sample a plurality of locations within a single suspected region. It is contemplated that this automated system may include the capability to predefine the step size between biopsy locations (e.g., how large a distance will separate successive biopsy samples). It is contemplated that this automated system may include the capability to predefine a shape of a region to be repeatedly sampled (e.g., a curvilinear region, a circular region, a square region, or a region having a shape defined by numerical coordinates relative to an initial biopsy site). It is contemplated that this automated system may include the capability to determine the order in which successive biopsy samples will be procured, so that each sample can be identified, for example by an ordinal number, as to the location from location that sample was procured.

Such automated systems can be provided using purely mechanical apparatus, which can be operated by hand, wherein all of the motions or steps other than the initial insertion of the needle into a patient at a site to be biopsied and the retraction of the needle after the specimen or specimens that are desired to be procured have been taken are performed in response to a command, such as depressing a button or a trigger. In an alternative embodiment, such automated systems can be provided that use a general purpose programmable computer operating under the control of instructions recorded in a non-transitory manner on a machine readable medium to control the operational motions or steps.

In some embodiments the inner diameter of the distal end of a needle tip can be less than 400 microns, less that 300 microns, or less than 200 microns. In some embodiments the needle tip is capable of collecting samples of intact tissue having lengths up to the length of a forward thrust of the needle.

It is well known in the field that a "stylet" is sometimes used in conjunction with a front-end biopsy device. A stylet is a solid cylindrical wire whose dimensions match those of the inner surface of the needle. The step-out of the current invention, and a back-facing barb, define the geometry of a stylet for this invention. A stylet is understood to be able to be inserted through the proximal luer-lock type fitting (40) in a proximal to distal direction to extend past the distal most end of cutting surface (60) to block the distal collection chamber (80). The stylet can be removed after a needle has been advanced to an optimal position to begin collecting a sample. A stylet is also sometimes used to express the sample out of the front end.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A microbiopsy needle tip, consisting of:
   a tubular elongate structure having a proximal end and a distal end, said distal end having an outer diameter OD in the range from an outer diameter of a 22 gauge needle to an outer diameter of a 27 gauge needle and defining an aperture having a circular cross section centered on a central axis of said tubular elongate structure, said aperture having an inner diameter ID1 at said distal end and an inner diameter ID2 at a distance in a proximal direction along said central axis, wherein said inner diameter ID2 is larger than said inner diameter ID1;
   said distal end having at least three sharpened points projecting axially therefrom and having at least three points of attachment to said tubular elongate structure, wherein at each of the at least three points of attachment two of said at least three sharpened points meet, said at least three sharpened points confined dimensionally within an annulus defined by said outer diameter OD and said inner diameter ID1, said at least three sharpened points defining cutting surfaces, said cutting surfaces joining at said at least three points of attachment to said tubular elongate structure, said tubular elongate structure having a distal collection portion with said inner diameter ID1;
   said tubular elongate structure having a step-out, wherein said tubular elongate structure has said inner diameter ID2 for a distance along said central axis in a proximal direction so as to define a proximal collection portion with said inner diameter ID2;
   said microbiopsy needle tip being capable of procuring a biopsy specimen of intact tissue having a diameter substantially equal to said inner diameter ID1 and retaining said biopsy specimen within said proximal collection portion for later recovery, wherein said distal collection portion is characterized by a length of less than 10 mm.

2. The microbiopsy needle tip of claim 1, wherein said outer diameter OD is the outer diameter of a 25 gauge needle.

3. The microbiopsy needle tip of claim 2, wherein said distal collection portion is characterized by a length between 1 mm and 4 mm.

4. The microbiopsy needle tip of claim 1, wherein said aperture extends along said central axis of said tubular elongate structure from said proximal end to said distal end.

5. The microbiopsy needle tip of claim 1, wherein said tubular elongate structure is capable of being curved so as to sample multiple biopsy sites in close proximity without retracting and reintroducing said microbiopsy needle tip.

6. A microbiopsy needle tip, consisting of:
   a tubular elongate structure having a proximal end and a distal end, said distal end having an outer diameter OD in the range from an outer diameter of a 22 gauge needle to an outer diameter of a 27 gauge needle and defining an aperture having a circular cross section centered on a central axis of said tubular elongate structure, said aperture having an inner diameter ID1 at said distal end and an inner diameter ID2 at a distance in a proximal direction along said central axis, wherein said inner diameter ID2 is larger than said inner diameter ID1;
   said distal end having at least three sharpened points projecting axially therefrom and having at least three points of attachment to said tubular elongate structure, wherein at each of the at least three points of attachment two of said at least three sharpened points meet, said at least three sharpened points confined dimensionally within an annulus defined by said outer diameter OD and said inner diameter ID1, said at least three sharpened points defining cutting surfaces, said cutting surfaces joining at said at least three points of attachment to said tubular elongate structure, said tubular elongate structure having a distal collection portion with said inner diameter ID1;
   said tubular elongate structure having a step-out, wherein said tubular elongate structure has said inner diameter ID2 for a distance along said central axis in a proximal direction so as to define a proximal collection portion with said inner diameter ID2;
   said microbiopsy needle tip being capable of procuring a biopsy specimen of intact tissue having a diameter substantially equal to said inner diameter ID1 and retaining said biopsy specimen within said proximal collection portion for later recovery, wherein
   said tubular elongate structure comprises a proximal-facing bevel tip deposed between said distal collection portion with said inner diameter ID1 and said proximal collection portion with said inner diameter ID2, and said distal collection portion is characterized by a length of less than 10 mm.

7. The microbiopsy needle tip of claim 6, wherein said outer diameter OD is the outer diameter of a 25 gauge needle.

8. The microbiopsy needle tip of claim 7, wherein said distal collection portion is characterized by a length between 1 mm and 4 mm.

9. The microbiopsy needle tip of claim 6, wherein the aperture extends along said central axis of said tubular elongate structure from said proximal end to said distal end.

10. The microbiopsy needle tip of claim 6, wherein said tubular elongate structure is capable of being curved so as to sample multiple biopsy sites in close proximity without retracting and reintroducing said microbiopsy needle tip.

11. A microbiopsy needle tip, comprising:
    a tubular elongate structure having a proximal end and a distal end, said distal end having an outer diameter OD in the range from an outer diameter of a 22 gauge needle to an outer diameter of a 27 gauge needle and defining an aperture having a circular cross section centered on a central axis of said tubular elongate structure, said aperture having an inner diameter ID1 at said distal end and an inner diameter ID2 at a distance in a proximal direction along said central axis, wherein said inner diameter ID2 is larger than said inner diameter ID1;

said distal end having at least three sharpened points projecting axially therefrom and having at least three points of attachment to said tubular elongate structure, wherein at each of the at least three points of attachment two of said at least three sharpened points meet, said at least three sharpened points confined dimensionally within an annulus defined by said outer diameter OD and said inner diameter ID1, said at least three sharpened points defining cutting surfaces, said cutting surfaces joining at said at least three points of attachment to said tubular elongate structure, said tubular elongate structure having a distal collection portion with said inner diameter ID1;

said tubular elongate structure having a step-out, wherein said tubular elongate structure has said inner diameter ID2 for a distance along said central axis in a proximal direction so as to define a proximal collection portion with said inner diameter ID2;

wherein said tubular elongate structure is capable of being curved so as to sample multiple biopsy sites in close proximity without retracting and reintroducing the needle tip, said microbiopsy needle tip being capable of procuring a biopsy specimen of intact tissue having a diameter substantially equal to said inner diameter ID1 and retaining said biopsy specimen within said proximal collection portion for later recovery, wherein said distal collection portion is characterized by a length of less than 10 mm.

* * * * *